US011439525B2

(12) United States Patent
Goetz et al.

(10) Patent No.: US 11,439,525 B2
(45) Date of Patent: *Sep. 13, 2022

(54) IMPLANT DELIVERY DEVICE ADAPTED TO BE ATTACHED TO OR INTERCONNECTED WITH A CATHETER, CATHETER AND METHOD

(71) Applicant: VENUS MEDTECH (HANGZHOU), INC., Zhejiang (CN)

(72) Inventors: Wolfgang Goetz, Regensberg (DE); Hou-Sen Lim, Singapore (SG)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 308 days.

This patent is subject to a terminal disclaimer.

(21) Appl. No.: 16/549,278

(22) Filed: Aug. 23, 2019

(65) Prior Publication Data
US 2020/0046530 A1    Feb. 13, 2020

Related U.S. Application Data

(63) Continuation of application No. 13/579,919, filed on Dec. 27, 2012, now Pat. No. 10,390,981.

(51) Int. Cl.
*A61F 2/95* (2013.01)
*A61F 2/24* (2006.01)

(52) U.S. Cl.
CPC ............ *A61F 2/95* (2013.01); *A61F 2/2439* (2013.01); *A61F 2/2412* (2013.01); *A61F 2002/9511* (2013.01); *A61F 2250/006* (2013.01)

(58) Field of Classification Search
CPC .......... A61F 2/95; A61F 2/2439; A61F 2/243; A61F 2/2436; A61F 2/2412; A61F 2/2427; A61F 2002/9511; A61F 2002/9505; A61F 2250/006; A61B 2002/0072
See application file for complete search history.

(56) References Cited

U.S. PATENT DOCUMENTS

| 4,878,906 A | 11/1989 | Lindemann et al. |
| 5,263,969 A | 11/1993 | Phillips |
| 5,456,713 A | 10/1995 | Chuter |
| 5,554,183 A | 9/1996 | Nazari |
| 5,713,948 A | 2/1998 | Uflacker |
| 5,948,017 A | 9/1999 | Taheri |
| 5,957,929 A | 9/1999 | Brenneman |
| 6,168,616 B1 | 1/2001 | Brown, III |
| 6,740,111 B1 | 5/2004 | Lauterjung |
| 6,764,503 B1 | 7/2004 | Ishimaru |
| 7,041,132 B2 | 5/2006 | Quijano et al. |

(Continued)

FOREIGN PATENT DOCUMENTS

| CA | 2 715 195 | 9/2009 |
| CN | 101049271 A | 10/2007 |

(Continued)

*Primary Examiner* — Alexander J Orkin
(74) *Attorney, Agent, or Firm* — Raymond Sun

(57) ABSTRACT

The present invention relates to a device (3) intended to be attached to or interconnected with a medical implant (1), and intended to be attached to or interconnected with a catheter (5), the catheter (5) being intended for implanting the implant (1). The invention further relates to a catheter (5) suited for receiving at least one such device (3) and to a method.

20 Claims, 3 Drawing Sheets

(56) References Cited

U.S. PATENT DOCUMENTS

Figure 1:
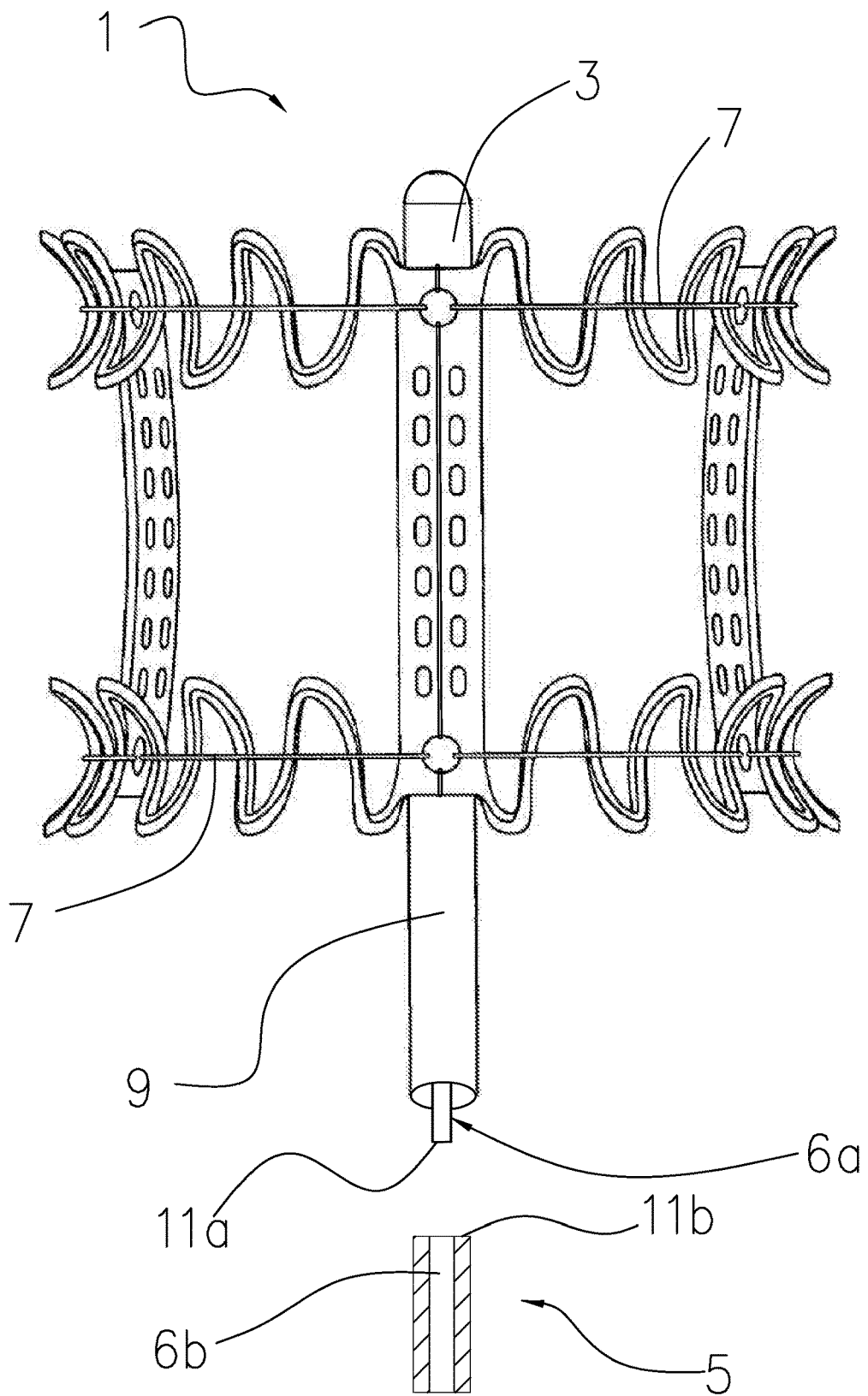

| | | |
|---|---|---|
| 10,390,981 B2 * | 8/2019 | Goetz .................. A61F 2/95 |
| 2003/0050694 A1 | 3/2003 | Yang et al. |
| 2004/0034411 A1 | 2/2004 | Quijano et al. |
| 2004/0138734 A1 | 7/2004 | Chobotov et al. |
| 2004/0147939 A1 | 7/2004 | Rabkin et al. |
| 2005/0203615 A1 | 9/2005 | Forster et al. |
| 2006/0212110 A1 | 9/2006 | Osborne et al. |
| 2006/0259119 A1 | 11/2006 | Rucker |
| 2007/0061008 A1 * | 3/2007 | Salahieh .................. B65B 5/04 623/2.11 |
| 2007/0100427 A1 | 5/2007 | Perouse |
| 2007/0203561 A1 | 8/2007 | Forster et al. |
| 2007/0233223 A1 | 10/2007 | Styrc |
| 2008/0103581 A1 | 5/2008 | Goto |
| 2008/0234797 A1 | 9/2008 | Styrc |
| 2008/0262592 A1 | 10/2008 | Jordan et al. |
| 2009/0005863 A1 | 1/2009 | Goetz et al. |
| 2009/0192586 A1 | 7/2009 | Tabor et al. |
| 2009/0228093 A1 | 9/2009 | Taylor et al. |
| 2013/0245752 A1 | 9/2013 | Goetz et al. |

FOREIGN PATENT DOCUMENTS

| | | |
|---|---|---|
| EP | 0985 424 A1 | 3/2000 |
| JP | 1999509450 | 8/1999 |
| JP | 2001095810 | 4/2001 |
| JP | 2006521161 | 9/2006 |
| JP | 2009528089 | 8/2009 |
| WO | WO1997/003624 | 2/1997 |
| WO | WO 2008/029296 | 3/2008 |
| WO | WO2009/109348 | 9/2009 |

* cited by examiner

IMPLANT DELIVERY DEVICE ADAPTED TO BE ATTACHED TO OR INTERCONNECTED WITH A CATHETER, CATHETER AND METHOD

The present invention relates to a device intended to be attached to or interconnected with a catheter according to claim 1. The invention further relates to a catheter according to claim 7 suited for receiving at least one such device and a method according to claim 11.

In a number of patients, certain body functions have to be carried out or supported by means of implants. In order to facilitate the delivery of the implants to the implantation site within a patient's body, the implants are often attached to mechanical devices such as catheters.

It is one object of the present invention to provide a device and a method for attaching or interconnecting a medical implant with a catheter. According to a further aspect, a catheter comprising at least one such device and a method are to be provided.

The object of the invention is solved by means of a device according to claim 1. According to another aspect of the invention, a catheter comprising the feature combination of claim 7 and a method according to claim 11 are provided.

In particular, the device according to the invention is intended to be attached to or interconnected with a medical implant and intended to be attached to or interconnected with a catheter.

Embodiments can include one or more of the following features.

The device according to the invention can be temporarily or permanently or detachably attachable to or interconnectable with the medical implant. The device according to the invention can be temporarily or permanently or detachably attachable to or interconnectable or connected, respectively, with the catheter. The catheter is intended for implanting the implant.

The term "catheter"—in the sense of the present invention—is used by way of example for any delivery implement or device for delivering the medical implant to the implantation site. Hence, the term is not to be understood to relate only to catheters—rather, any suitable device for advancing an implant to its implantation site is also contemplated.

The device can be mainly or partly tube-shaped. As such, the device can have a circular or oval cross-section. However, the device may also have any other cross-section apt for establishing a connection between the device and the catheter according to the invention.

As regards the implant, the device according to the invention does not have to be designed in a particular way as long as the implant can be temporarily or permanently or detachably fixed at or onto the device according to the invention.

In some embodiments according to the invention, the device according to the invention detachably comprises the implant.

The implant can be of any type that is known to a person skilled in the art for supporting or carrying out functions of a patient's body. Examples include implants such as heart valves, substitutes or replacement of heart valves, stents for holding vessels or other body tubes open, and the like.

The implant may be of an expandable and/or (again) foldable or collapsible, respectively, type as is described together with the implementation thereof as such in great detail in WO 2008/029296 A2 ("Minimally invasive heart valve replacement", filed on Feb. 15, 2007) to the inventors of the present invention, and also in WO 2009/109348 A1 ("Stent, welcher vom expandierten Zustand kontrolliert erneut im Durchmesser verringerbar ist", filed on Mar. 2, 2009) also to the inventors of the present invention.

In some embodiments, the implant is foldable and/or unfoldable and comprises first folding and/or unfolding means adapted and/or intended or configured for folding and/or unfolding the implant.

In certain embodiments, the implant is intended to be attached to or interconnected with the device by means of crimping. That is, the device is intended to have the implant crimped thereon, or the implant has already been crimped onto the device.

The first folding and/or unfolding means are guided around certain portions of the implant that can be tightened or released.

The first folding and/or unfolding means can be arranged at or at least in connection with the implant such that it is or they are, respectively, operatively connected with the implant. The first folding and/or unfolding means can be arranged such that they can contribute to or effect the folding and/or unfolding of the implant which is attached to the device according to the invention. The folding and/or unfolding of the implant by use of the first folding and/or unfolding means can be effected when a force, a tension or stress or strain is applied or put, onto the first folding and/or unfolding means or rather released from the first folding and/or unfolding means. Such a tension, stress or strain can, for example, be induced or generated by an actuating device (e.g., a pulling device) which can be operated by a user.

In some embodiments according to the invention, it can be intended to use at least the first folding and/or unfolding means of the implant to establish a connection such as a form closure connection between the device according to the invention and the catheter.

The first folding and/or unfolding means of the implant can pass through an inner space of the device.

In some embodiments of the present invention, the inner space is an opening that extends along the whole or entire length of the device according to the invention, i.e. from a distal end to a proximal end thereof. In other embodiments, the inner space is arranged in a longitudinal direction of the device and extends at least from a front end opening of the device (be it the proximal or the distal end of the device) to a second opening which is an outlet of the first folding and/or unfolding means.

The first folding and/or unfolding means of the implant can be arranged such that they leave the device according to the invention through at least one opening of the device. Such an opening may be provided at one end of the device according to the invention.

However, the first folding and/or unfolding means can leave the device according to the invention at any other suitable position. The first folding and/or unfolding means can leave the device according to the invention all through the same opening, however, some of the first folding and/or folding means can also leave the device according to the invention through different openings.

In some embodiments according to the invention, the first folding and/or unfolding means can comprise one or more reins or threads or strings or can consist thereof.

In certain embodiments according to the invention, the device according to the invention comprises attaching or interconnecting means. Such attaching or interconnecting means are intended and provided for attaching or interconnecting the device according to the invention to a catheter. The attaching or interconnecting means can assist or support the attachment or interconnection of the device according to the invention with the catheter.

In some embodiments according to the invention, the attaching or interconnecting means are arranged at or within the device according to the invention. Examples include lugs or noses or the like, but also recesses or notches or the like which are arranged in an inner space of the device according to the invention in such a way that they favour the attachment or interconnection of the device according to the invention with the catheter. However, the device does not have to comprise particularly formed geometrical shapes.

For example, in order to establish a preferably tight or firm connection, the device according to the invention can comprise male faces or terminals and the catheter can comprise female faces or terminals or vice versa. As such, the connection between the device according to the invention and the catheter can resemble or be a plug-in connection.

In certain embodiments according to the invention, the device according to the invention is a catheter tip. During preparation of implanting the implant attached to the device according to the invention by use of the catheter, the device, the catheter tip or the like can be attached to or interconnected with the catheter in situ, for example, in the operating room or theatre, by, for example, merely slipping or snapping on the catheter tip onto the catheter.

In some embodiments according to the invention, the catheter according to the present invention is suited and/or configured or prepared for receiving at least one such device according to the invention.

In certain embodiments according to the invention, the catheter according to the invention comprises at least one device according to the invention.

The catheter can be mainly or partly tube-shaped. As such, the catheter can have a circular or oval cross-section. However, the catheter can have any other cross-section apt for establishing a connection between the catheter and the device according to the invention. The catheter can be a catheter shaft.

In some embodiments, the catheter comprises attaching or interconnecting means for being attached to or interconnected with the device according to the invention. Such attaching or interconnecting means can include lugs or noses or the like, but also recesses or notches or the like. The interconnecting means can be arranged in an inner space of the catheter or at an outer surface or any other part thereof. The catheter may have any particularly formed geometrical shapes. The attaching or interconnecting means of the catheter can form complements or counter pieces, respectively, to the attaching or interconnecting means of the device.

Furthermore, in certain embodiments of the invention, the catheter comprises second folding and/or unfolding means.

In certain embodiments according to the present invention, these second folding and/or unfolding means can contribute to or effect an interconnection or attachment of the implant to the device according to the invention.

In certain embodiments according to the invention, the second folding and/or unfolding means is interconnected with or attached to the first folding and/or unfolding means of the implant. The second folding and/or unfolding means can be embodied as reins, threads or strings or the like.

In some embodiments according to the present invention, the second folding and/or unfolding means is made of wire (or comprises a wire). In other embodiments according to the invention, the second folding and/or unfolding means is not made of wire (nor comprises it one).

In some embodiments according to the invention, the second folding and/or unfolding means is operatively connected to the first folding and/or unfolding means of the implant.

In particular embodiments according to the invention, the second folding and/or unfolding means is operatively connected to the first folding and/or unfolding means of the implant to remain connected until the catheter is withdrawn from the patient's body after completion of the implantation of the implant. That is, in these embodiments, the implant is released from the device according to the invention and/or from the catheter, by disconnecting the device according to the invention from the implant (or by releasing the implant from the device according to the invention) at a site that is different to a connection site where the first and the second folding and/or unfolding means had been connected to each other. In these embodiments, the catheter according to the invention may comprise a separating means to separate or to release (e.g., to cut or to disconnect) the implant from the first and/or the second folding and/or unfolding means at a site different to the site where the first and the second folding and/or unfolding means had been connected with each other.

In some embodiments according to the invention, both the first and the second folding and/or unfolding means are intended to remain with the catheter after release of the implant from the catheter.

In certain embodiments according to the invention, different folding and/or unfolding means are differently colour coded, or they have matching connectors of different shape, or they have different lengths or a combination of such features to avoid a wrong and possibly adverse connection.

In certain embodiments according to the invention, the second folding and/or unfolding means contributes to folding and/or unfolding the implant by means of the first folding and/or unfolding means in that they can transmit a force such as a tension or stress from an actuating device operated by a user to the implant. Usually, such an actuating device is arranged at a proximal end of the catheter as regards a user, such as, for example a tool holder or a handle, wherein the implant is arranged at the distal end of the catheter as regards the user.

In certain embodiments, the second folding and/or unfolding means are knotted or interloped with the first folding and/or unfolding means. In other certain embodiments, hook and eye connections are used to interconnect the first and the second folding and/or unfolding means. However, the design or construction of the connection between the first and the second folding and/or unfolding means is not restricted to a particular design. As long as the intended connection between the first and the second folding and/or unfolding means is achieved, any design or construction apt for this purpose is contemplated.

According to the present invention, a method according to the invention serves for loading or providing a delivery implement with an implant before implantation, wherein the method comprises attaching or fixing a device according to the invention comprising an implant onto a delivery implement.

In some embodiments of the method according to the invention, the implant is released from the device and/or from the catheter according to the invention by disconnecting the device according to the invention at a site that is different from a connection site at which the first and the second folding and/or unfolding means had been connected to each other (before implantation). In some of these embodiments, appropriate means for separating the implant from the device or from the catheter (i.e. by cutting of strings) may be used.

The attachment or fixation of the device according to the invention to or onto the delivery implement such as a catheter, in particular a catheter according to the invention, can be performed at any desired or required point of time. In some embodiments according to the invention, the device is attached or fixed to the delivery implement in the operation room or theatre or a the bedside.

Along with advantages that are obvious to the skilled one, the embodiments may provide one or more of the following advantages.

By using the device according to the invention, the present invention provides a simple option for attaching or interconnecting an implant to a catheter at any desired or required point of time, in particular in situ in the operating room just before implanting the implant.

As medical implants can also partly or entirely consist of living tissue, such as for example, pig heart valves, it may be recommended to keep the living tissue in fluid environment during storage or transport.

However, at least due to its mechanical structure, the catheter as a whole should not be stored or transported under wet conditions.

With the present invention, it is advantageously possible to store and/or transport the implant and the catheter separate from each other in best suitable environments.

In some embodiments according to the invention, it is possible to assemble them for the purpose of implanting in a relative short time and in an uncomplicated manner. For example, in certain embodiments of the invention, a cumbersome assembling of strings and implant right before implantation, e.g., at the bedside, can advantageously be avoided.

In this way, it is advantageously possible to store and/or transport the catheter in a, for example, dry environment suitable for the sensitive mechanical structure of the catheter; and to store and/or transport the implant under wet or humid conditions in order to keep its biological tissue in a humid condition. Thus, possible damages of the mechanical structure of the catheter can advantageously be avoided. The biological tissue does not dry out.

The device according to the invention can be designed or constructed such that it is not susceptible for being damaged or destroyed by fluids such as liquids surrounding the implant. As such, it is advantageously also possible to interconnect the device according to the invention and the implant before storage or transportation. In particular, due to the separation of catheter and device (tip of the catheter, for example), both the catheter and the device can be produced from different materials, in different processes and the like. Each can thus be manufactured to its best, independently of the need of the other part.

Due to the attaching or interconnecting means of the device according to the invention, it is advantageously possible to establish or achieve a simple and uncomplicated connection between the device and the catheter.

Due to simply establishing a connecting between the first folding and/or unfolding means of the implant and the second folding and/or unfolding means of the catheter, it is advantageously simply and in an uncomplicated manner possible to transfer the required force for folding and/or unfolding the implant from an actuating device of the user to the implant.

Other aspects, features, and advantages will be apparent from the description, figures and claims.

In the following, the invention is further explained by means of the figures of the drawing. However, the invention must not be limited to the examples explained by means of the figures.

Figure 2:
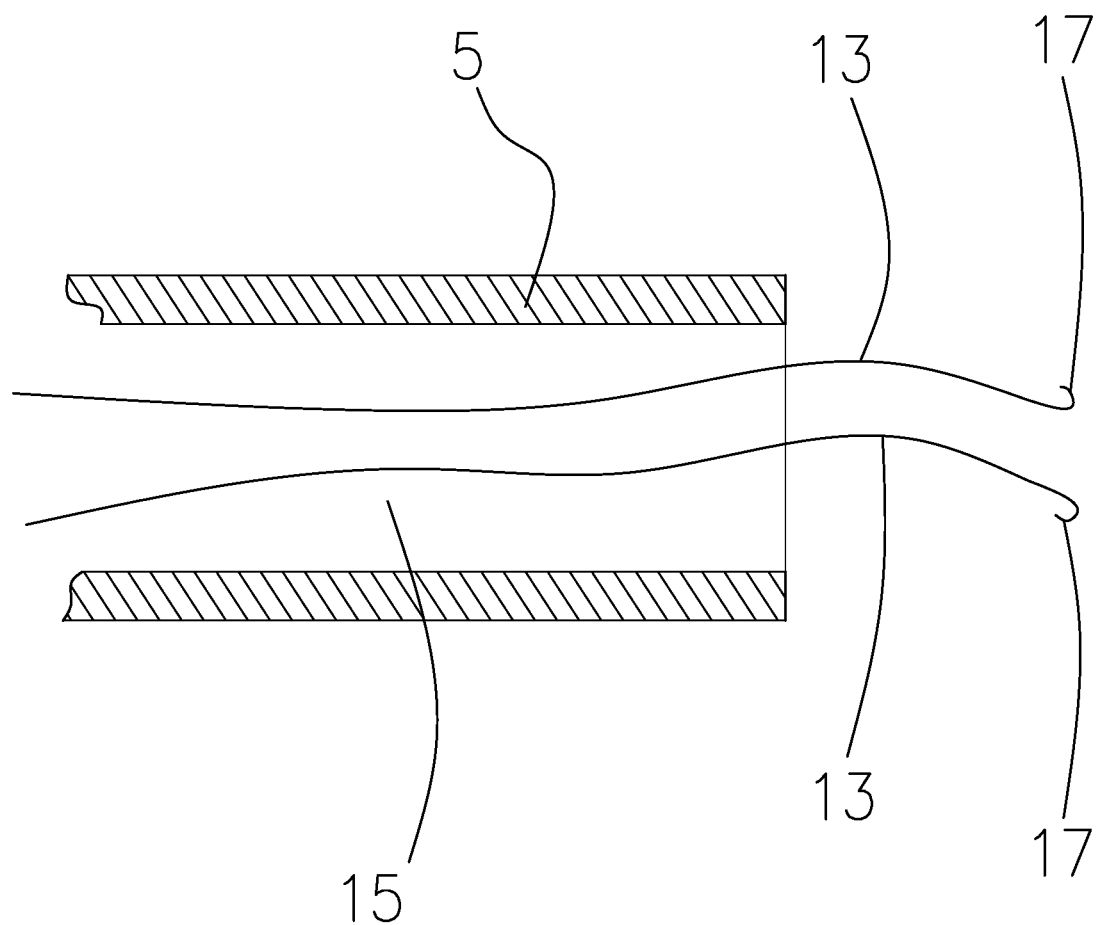
Figure 3:
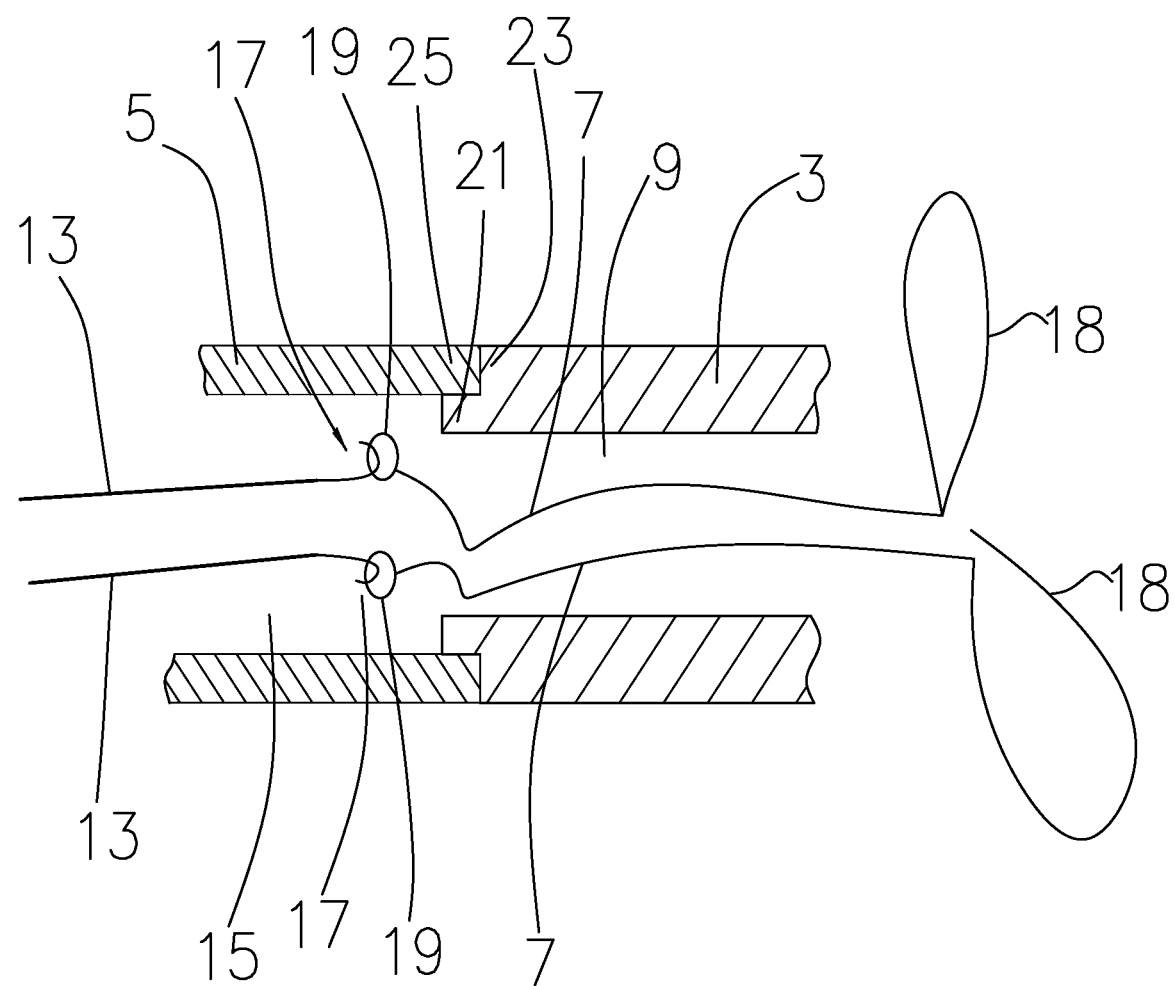

FIG. 1 shows a device according to the invention comprising an implant;

FIG. 2 schematically shows a catheter comprising second folding and/or unfolding means; and FIG. 3 schematically shows a connection state between the catheter and the device according to the invention.

FIG. 1 shows an implant 1, viewed from the side, in an expanded state. The implant 1 is connected to a device 3 according to the invention. The device 3 is designed in form of a catheter tip.

At the lower end of FIG. 1, a part of a catheter 5 is shown. The catheter 5 is detached from the device 3.

The device 3 comprises first interconnection means 6a. The catheter 5 comprises second interconnection means 6b.

The device 3 and/or the implant 1 comprise first folding and/or unfolding means 7. The first folding and/or unfolding means 7 can be embodied as strings.

The first folding and/or unfolding means 7 of the implant 1 pass through an inner space 9 of the device 3. The first folding and/or unfolding means leave (not shown) the device 3 according to the invention through an opening 11a. In FIG. 1, opening 11a is arranged at the lower end of the device 3 according to the invention which is directed to the catheter 5. The first folding and/or unfolding means may enter into the catheter 5 through an opening 11b of catheter 5.

FIG. 2 shows a catheter 5 according to the invention comprising second folding and/or unfolding means 13. The second folding and/or unfolding means 13 are arranged in an inner space 15 of catheter 5.

The second folding and/or unfolding means 13 can be embodied as strings. At one end (in FIG. 2 at the right-hand end), the second folding and/or unfolding means 13 comprise hooks 17. The hooks 17 are provided for establishing an interconnection to the first folding and/or unfolding means 7 of the implant (not shown in FIG. 2). It is noted that FIG. 2 shows a state of the catheter 5 before being connected to the device (not shown in FIG. 2) according to the invention.

FIG. 3 shows a connection state between the catheter 5 and the device 3 according to the invention.

In the inner space 9 of device 3, the first folding and/or unfolding means 7 of implant 1 (not shown here) are arranged. The first folding and/or unfolding means 7 comprise loops 18 for surrounding the implant (not shown in FIG. 3) and also loops or eyes 19 provided for establishing an interconnection with the second folding and/or unfolding means 13 of catheter 5. As exemplified here, the connection between the first and the second folding and/or unfolding means 7, 13 could be established by hooking hooks 17 into eyes 19.

As is shown in FIG. 3, device 3 comprises attaching or interconnecting means such as a nose 21 and a recess 23 forming an offset for receiving a blunt end 25 of catheter 5. Blunt end 25 of catheter 5 is an example for an attaching or interconnecting means of catheter 5.

The connection between device 3 and catheter 5 can be achieved by simply slipping on device 3 onto catheter 5 such as a plug-in connection. An additional frictional closure may be provided.

As is obvious to the skilled person, the invention is, of course, not limited to plug-in or slipping or snatching connections as exemplified here. Any other suitable interconnection is also contemplated.

The invention claimed is:

1. An interventional heart valve delivery assembly, comprising:
   a tube having an axial length, opposite proximal and distal ends, and having a first lumen extending continuously from the proximal end to the distal end;
   an implant having an axial length and releasably attached around the tube and having opposite proximal and distal ends, wherein the tube extends through a central portion of the implant, with the distal end of the tube extending to the distal end of the implant, and wherein the axial length of the implant is less than the axial length of the tube; and
   a catheter detachably connectable to the proximal end of the tube via a tight or firm connection, wherein the tube is longitudinally non-slidable relative to the catheter after being connected to the catheter,
   wherein the catheter has a second lumen in communication with the first lumen of the tube when the catheter is connected to the tube,
   wherein the implant is foldable and/or unfoldable, and comprises a first folding and/or unfolding member for folding and/or unfolding the implant, and the catheter comprises a second folding and/or unfolding member interconnected with or attached to the first folding and/or unfolding member of the implant, and
   wherein the implant is detachable at an implantation site from the tube which is configured to remain connected to the catheter.

2. The interventional heart valve delivery assembly according to claim 1, wherein the proximal end and the distal end of the tube respectively extend beyond the proximal end and the distal end of the implant respectively.

3. The interventional heart valve delivery assembly according to claim 1, wherein the implant has a stent entirely located outside the first lumen of the tube.

4. The interventional heart valve delivery assembly according to claim 3, wherein the stent of the implant is entirely located outside the second lumen of the catheter.

5. The interventional heart valve delivery assembly according to claim 1, wherein the distal end of the tube with its first lumen extends beyond the distal end of the implant.

6. The interventional heart valve delivery assembly according to claim 1, wherein the first folding and/or unfolding member extends at least partially in the first lumen of the tube.

7. The interventional heart valve delivery assembly according to claim 6, wherein the second folding and/or unfolding member extends at least partially in the second lumen of the catheter.

8. The interventional heart valve delivery assembly according to claim 7, wherein the second folding and/or unfolding member contributes to folding and/or unfolding the implant by member of the first folding and/or unfolding member in that they are able to transmit a force from an actuating tube operated by a user to the implant.

9. The interventional heart valve delivery assembly according to claim 1, wherein at least one of the first folding and/or unfolding member and the second folding and/or unfolding member comprises one or more reins, threads, or strings.

10. The interventional heart valve delivery assembly according to claim 1, wherein the catheter is connected to the tube by an attaching or interconnecting mechanism, which is selected from a group consisting of: lug, nose, recess, and notch.

11. A method for delivering the interventional heart valve delivery assembly according to claim 1 to a patient's heart valve, comprising:
    attaching the implant to the tube via a first folding and/or unfolding member for folding or unfolding the implant;
    attaching the tube and the implant to the catheter with the first lumen of the tube communicating with the second lumen of the catheter, wherein the tube is longitudinally non-slidable relative to the catheter after attaching to the catheter;
    connecting a second folding and/or unfolding member to the first folding and unfolding member;
    delivering the catheter with the tube and the implant to the patient's heart valve;
    releasing the implant from the tube by separating the implant from the first folding and/or unfolding member; and
    withdrawing the catheter with the tube.

12. The method according to claim 11, wherein the second folding and/or unfolding member extends at least partially in the second lumen and the first folding and/or unfolding member extends at least partially in the first lumen.

13. The method according to claim 11, wherein both the first folding and/or unfolding member and the second folding and/or unfolding member remain with the catheter and the tube after release of the implant from the tube.

14. The method according to claim 11, wherein the tube is attached to the catheter via a snap-on connection.

15. The method according to claim 11, wherein the tube is attached to the catheter by slipping on the tube onto the catheter with a plug-in connection.

16. The method according to claim 15, wherein an additional frictional closure is provided between the tube and the catheter after attaching the tube to the catheter.

17. The method according to claim 11, wherein before attaching the tube and the implant to the catheter, the catheter and the tube are separately stored, the catheter is stored in a dry condition, and the tube with the implant is stored in a wet or humid condition.

18. The method according to claim 11, wherein the tube is attached to the catheter in an operating room or nearby.

19. The method according to claim 11, wherein at least one of the first folding and/or unfolding member and the second folding and/or unfolding member comprises one or more reins, threads, or strings.

20. A method for delivering the interventional heart valve delivery assembly to a patient's heart valve, the interventional heart valve delivery assembly comprising:
    a tube having a first lumen, and having opposite proximal and distal ends;
    a cylindrical implant releasably attached around the tube and having opposite proximal and distal ends, wherein the tube extends through a central portion of the implant, with the distal end of the tube extending to the distal end of the implant; and
    a catheter detachably connectable to the proximal end of the tube via a tight or firm connection,
    wherein the catheter has a second lumen in communication with the first lumen of the tube when the catheter is connected to the tube,
    wherein the method comprises:
    attaching the implant to the tube via a first folding and/or unfolding member for folding or unfolding the implant;
    attaching the tube and the implant to the catheter with the first lumen of the tube communicating with the second lumen of the catheter, wherein the tube is longitudinally non-slidable relative to the catheter after attaching to the catheter;

connecting a second folding and/or unfolding means to the first folding and unfolding means, wherein the second folding and/or unfolding member extends at least partially in the second lumen and the first folding and/or unfolding member extends at least partially in the first lumen;

delivering the catheter with the tube and the implant to the patient's heart valve;

releasing the implant from the tube by separating the implant from the first folding and/or unfolding member; and withdrawing the catheter with the tube.

* * * * *